United States Patent [19]

Orndorff

[11] Patent Number: 4,677,072

[45] Date of Patent: Jun. 30, 1987

[54] RHODOTORULA HAVING DESATURASE ENZYMES

[75] Inventor: Steve A. Orndorff, Rockville, Md.

[73] Assignee: Westvaco Corporation, New York, N.Y.

[21] Appl. No.: 707,015

[22] Filed: Feb. 28, 1985

[51] Int. Cl.[4] .................. C12N 1/16; C12N 9/02; C12P 7/64; C12R 1/645

[52] U.S. Cl. .................. 435/255; 435/34; 435/134; 435/189; 435/911

[58] Field of Search .............. 435/34, 134, 189, 255

[56] References Cited

U.S. PATENT DOCUMENTS

| | | | |
|---|---|---|---|
| 3,115,442 | 12/1963 | Wallen | 195/30 |
| 3,359,177 | 12/1967 | Takashi et al. | 195/28 |
| 3,619,372 | 11/1971 | Yoshida et al. | 195/66 R |
| 3,709,783 | 1/1973 | Tanaka et al. | 195/28 R |
| 3,764,473 | 10/1973 | Tanaka et al. | 195/28 R |
| 3,892,629 | 7/1975 | Smith et al. | 195/36 R |
| 3,966,553 | 6/1976 | Charpentier et al. | 195/28 R |
| 3,975,234 | 8/1976 | Hitzman | 195/28 |
| 4,281,064 | 7/1981 | Suzuki et al. | 435/134 |
| 4,340,671 | 7/1982 | Gibson | 435/32 |
| 4,485,172 | 11/1984 | Gierhart | 435/134 |

FOREIGN PATENT DOCUMENTS

| | | |
|---|---|---|
| 0062492 | 10/1982 | European Pat. Off. . |
| 2091286A | 7/1982 | United Kingdom . |
| 2091285A | 7/1982 | United Kingdom . |

OTHER PUBLICATIONS

Ohba et al, Biochimica et Biophysica Acta, vol. 572 (1979), pp. 352–362.
C. Yuan and K. Block, "Journal of Biological Chemistry", vol. 236, No. 5, May 1961, pp. 1277–1279.
DIFCO Manual, 9th edition, pp. 237–254.

*Primary Examiner*—Lionel M. Shapiro

[57] ABSTRACT

A yeast culture medium contains glucose, yeast extract, buffers, alkaline earth metal salts, and antibiotics, has a pH of 4.3 to 4.7. Yeast strains of the genus Rhodotorula, obtained from water and soil samples, are useful as desaturase enzymes, especially for the conversion of oleic acid to linoleic acid in improved yields using the yeast culture medium.

1 Claim, No Drawings

RHODOTORULA HAVING DESATURASE ENZYMES

FIELD OF THE INVENTION

This invention relates to desaturase yeast strains of the genus Rhodotorula which cause the desaturation of fatty acids such as the conversion of oleic acid to linoleic acid, and to methods for using the yeast strains of Rhodotorula with a novel yeast culture medium containing glucose, buffers, alkaline earth metal salts and antibiotics.

BACKGROUND OF THE INVENTION

Desaturase reactions such as the desaturation of oleic acid to linoleic acid, are known to be catalyzed by whole cells of some bacteria, fungi and yeast as a seondary metabolite reaction. These desaturase enzymes require oxygen, cofactors and an electron transport system. Therefore, the reaction using these materials can only be carried out in viable whole cells. Use of desaturase enzymes as in the reaction to convert oleic acid to linoleic acid, has been studied in animals, yeasts, algae, fungi and bacteria. It is known that yeasts tend to possess only mono- and diunsaturated acids of $C_{16}$ and $C_{18}$, whereas fungi, particularly the lower fungi, contain a rich variety of polyunsaturated fatty acids. The exact composition of the fatty acids produced depends on the relative activities of the various desaturase enzymes, temperature, cell growth rate, and nature of growth-limiting nutrients.

Polyunsaturated fatty acids, for example linoleic acid, which contains 18 carbon atoms and two sets of double bonds, and linolenic acid, which contains 18 carbon atoms and three sets of double bonds, are known to be produced from oleic acid by temperature-induced desaturase enzyme systems. Polyunsaturated fatty acids are almost exclusively incorporated into the cell wall where their low melting point better maintains optimal membrane functions. Psychrophilic yeasts show a higher proportion of polyunsaturates than oleic acid compared to mesophilic yeasts. These findings led to the discovery that the desaturase enzyme synthesis is hyperinduced in bacteria and yeasts initially cultured at 30° C. and shifted to 20° C. The induction of enzyme synthesis occurs within minutes of a temperature shift but is subject to rapid feedback inhibition once the polyunsaturate:saturate ratio in the cell wall has been optimized.

It is further known that oleic acid desaturation rates appear to be the highest among yeasts such as those of the genus Torulopsis, Candida, and Rhodotorula. The desaturation technique is an aerobic process requiring oxygen, ferrous iron, reduced pyridine nucleotides and an electron transport chain. The free fatty acid is not desaturated and olelylphospholipid is the preferred enzyme substrate. Linoleic acid is the principal polyunsaturated fatty acid although it may be further desaturated to linolenic acid if the cells are allowed to age significantly. Nearly all polyunsaturated fatty acids are incorporated into the cell wall in the form of triglycerides, and none are excreted by the cell. The double bonds in the unsaturated acids are in the cis configuration, and where more than one double bond is present, they are normally in methylene-interrupted sequence. The desaturase enzymes have a half-line of ca. 30 minutes at 20° C. and are inhibited by cyanide, azide, metal chelating agents, and reagents that react with sulhydryl or disulfide groups.

Substantial information and work involving these conversion processes, as well as the enzymes and culture mediums for production of the enzymes, are known in the art.

A publication by Yuan, the Journal of Biological Chemistry, Vol. 234, No. 5, May 1961, entitled "Conversion of Oleic Acid to Linoleic Acid" is an important article in this area. This publication discloses conversion of oleic acid to linoleic acid using species of the yeast Torulposis utilis, the specific strain used being ATCC 8205. These authors report that the yeast strain ATCC 8205 of the genus Torulopsis utilis is a lipid-rich yeast known to contain large amounts of linoleate and forms the linoleic acid efficiently from oleate.

U.S. Pat. No. 4,281,064, to Suzuki et al, 1981, discloses a process for producing lipids having a high linoleic acid content wherein fungi of Pellicularia genus are cultivated in a medium of a carbohydrate or vegetable fiber as a carbon source. The culture medium contained glucose $NH_4NO_3$, $KH_2PO_4$, $MgSO_4\ 7H_2O$, malt extract, yeast extract, $FeSO_4\ 7H_2O$, $CaCl_2.2H_2O$, $CuSO_4.5H_2O$, and $ZnSO_4.7H_2O$ in water.

U.S. Pat. No. 3,966,553 to Charpentier et al describes a process for manufacturing citric acid by aerobic culture of yeast strains in medium containing at least one n-paraffin by adding to the culture medium a nitrogenous heterocyclic organic compound. The yeast strains mentioned for use in this process include the genera Torulopsis, Candida, and Rhodotorula. Culture media utilized in this method include those which contain $KH_2PO_4$, magnesium sulfate, ammonium nitrate, calcium carbonate, ferric sulfate, manganese sulfate, yeast extract, and water. Similar disclosures are found in published European Application No. 062,492, published Oct. 13, 1982, wherein hydrocarbons are converted to oxidized derivatives by contacting the hydrocarbons with a species of Acinetobacter. In U. K. Patent Application Nos. 2,091,285A and 2,091,286A, published July 28, 1982, methods for the production of fats and oils are described wherein the fats and oils are synthesized using yeast cells capable of synthesizing the fats and oils in a growth medium containing carbon and nitrogen nutrients. Yeast strains of the genus Endomyces, Rhodotorula, Lipomyces and Rhodosporidium are mentioned. In Pat. No. 2,091,285A, culture media which contain a fatty acid in combination with $KH_2PO_4$, an emulsifier and antibiotic in water, are disclosed.

U.S. Pat. No. 3,115,442 to Wallen discloses the microbial production of 10-hydroxy-stearic acid using a culture medium containing yeast extract, potassium acid phosphate, magnesium sulfate and water, to which oleic acid is added. The microbe is a species of Pseudomonas. A similar disclosure is found in U.S. Pat. No. 3,975,234, which describes the enzymatic fermentation of a hydrocarbon or alcohol to produce a dicarboxylic acid using a mutant strain of the microorganism Torulopsis bombicola which has been grown on a hydrocarbon free media.

U.S. Pat. Nos. 3,709,783, 3,764,473, and 3,359,177 describe culture media and fermentation methods which include antibiotics for the production of nitrogen compounds such as proteins in U.S. Pat. No. 3,709,783, glutamic acid in U.S. Pat. No. 3,764,473 and nucleotides in U.S. Pat. No. 3,359,177. U.S. Pat. No. 4,340,671 to Gibson discloses an *E. coli* sensitivity broth which contains antibiotics.

U.S. Pat. No. 3,619,372 to Yoshida et al discloses a lipase which is acid resistant and comprises glutamic acid or similar material. The lipase is prepared by culturing *Torulopsis ernobii* ATCC 20000 in a liquid medium containing carbon, nitrogen and inorganic salts under an aerobic condition. Vegetable oils or fatty acids may be added to the medium, including oleic acid.

U.S. Pat. No. 3,892,629 describes processes for growing a fungus and producing critic acid using the fungus, *Aspergillus niger*, as well as other fungi, including species of Penicillium.

In a publication by Difco Laboratories, entitled "Difco Manual of Dehydrated Culture Media and Reagents for Microbiological and Clinical Laboratory Procedures", Tenth Edition, pps. 1135–1141, there are set forth a series of culture media for use in the study of yeasts and molds. Included in this study are broths which contain nitrates, phosphates, sulfates and the like, which are identified as Czapek Dox Broth and Czapek Solution Agar on page 257. On pages 1120–1123 is listed W. L. Nutrient Medium which includes yeast extracts, bacto-dextrose, salts of potassium, calcium and magnesium and iron, and manganese, as well as bacto-agar. Various other culture media are disclosed.

While substantial work has been done in this area, it is clear that a need remains in the art to provide methods and systems for isolating and culturing improved desaturase yeast strains which will provide greater yields of the desired products from reactions of this type.

SUMMARY OF THE INVENTION

It is accordingly one object of the present invention to provide new yeast strains of increased desaturase activity.

A further object of the invention is to provide novel yeast culture media with which the novel yeast strains having improved desaturase activity can be enriched and isolated for production of useful products.

A still further object of the present invention is to provide methods for the production of yeast strains of the genus Rhodotorula and novel yeast culture media for their use as novel yeast strains which have desaturase activity.

An even further object of the present invention is to provide methods for the introduction of additional double bonds into fatty acids for the production of useful materials using enzymatic methods.

Another object of the present invention is to provide methods for the production of improved yeast desaturase strains of the genus Rhodotorula and use of those yeast strains with a novel yeast culture medium for the conversion of oleic acid to linoleic acid. Other objects and advantages of the present invention will become apparent as the description thereof proceeds.

In one embodiment of the invention there is provided a method for the enrichment and isolation of novel yeast strains of the genus Rhodotorula, which comprises obtaining cultures from water and soil samples, screening those samples for desaturase activity by determining the cell yield of linoleic acid, and obtaining yeast strains which have improved desaturase activity, particularly for the conversion of oleic acid to linoleic acid.

Also provided by the present invention is a yeast culture media for the enrichment of yeast, which comprises basal salt and nutrient portions comprising glucose, yeast extract, buffering salts, and an antibiotic portion containing 1–10 mg. per 100 ml of broth, said yeast culture media having a pH in the range of about 4.3 to 4.7.

There is also provided by the present invention a method for the desaturation of polycarboxylic acids which comprises contacting said polycarboxylic acid with a microorganism of the genus Rhodotorula, said microorganism having improved desaturase activity. A specific embodiment of the present invention involves the conversion of oleic acid to linoleic acid by contacting said oleic acid with desaturase enzymes of the genus Rhodotorula said enzymes having the identifying characteristics and activity of the Rhodotorula strains identified as strain 238, and strain 371, which is deposited under ATCC No. 20837.

DESCRIPTION OF PREFERRED EMBODIMENT

This invention is concerned with a number of related procedures which result in novel yeast strains and procedures for the improved desaturation of fatty acids, particularly the conversion of oleic acid to linoleic acid.

In one embodiment, the invention concerns a novel microbiological culture medium. In another embodiment, the invention concerns processes for the selective enrichment and isolation of oleaginous lipid rich yeasts. It has been discovered according to the present invention that the use of a yeast cultural media formulation and enrichment process which inhibits the growth of bacteria and fungi while promoting the growth of oleaginous yeast in a single step provides substantial advantages. The combination of acid pH, bacterial and fungal antibiotics, fatty acids and carbon sources comprises a unique yeast culture medium. Further, the low temperature incubation of the inoculated culture media has been found to stimulate the fatty acid metabolism of the yeast, thereby producing a greater portion of oleaginous yeast in comparison with yields from other media and processes. Traditionally used microbiological enrichment culture procedures are laborious, time intensive and non-specific for the yeast. Moreover, numerous subcultures from an environmental sample must be made to isolate the yeast and it is very difficult to select and isolate an oleaginous yeast due to the interference of other microorganisms. In the present invention, substantial advantages are obtained, such as the more accurate quantitation of yeast in environmental samples, the single step enrichment for yeast, oleaginous yeast and yeast with the ability to emulsify fats and oils. The invention also provides advantages in the single step isolation of pure cultures of yeast from environmental samples, most of which are composed of mixed populations of microorganisms.

In the present invention, novel yeasts were developed through a screening process involving strains of lipid-rich yeast isolated from the selective enrichment broth cultures of water and soil samples. A novel selective culture medium was developed for this process. The culture medium and conditions for growth were found to be highly selective for the enrichment of oleaginous yeast from environmental samples containing mixed populations of microorganisms. A representative number of these yeast isolates were screened for desaturase activity from which there were obtained microorganisms which possessed high levels of linoleic acid, rapid growth rate and fatty acid emulsifying activity. The oleaginous yeasts were isolated in pure culture directly from soil and water samples using the novel selective enrichment culture medium and process. The enrichment medium was found to be superior to conventional culture media for the enrichment and isolation of yeasts from mixed populations of bacteria, yeast and fungi.

In production of the yeast, approximately 200 yeast cultures from the selective enrichment broth culture of the samples were screened for desaturase activity in order to obtain the yeast which had a linoleic acid content superior to those known in the art. Almost half of the isolates tested had higher linoleic acid contents than the known *Torulposis utilis* ATCC 8205, which is at present the most linoleic acid-rich yeast known. Two species of the genus Rhodotorula possessed 3 to 6 times higher desaturase activity and 3 to 7 times greater total fatty acid yield than the known *T. utilis* in liquid culture. The addition of oleic acid to the fermentation enhanced fatty acid and linoleic acid yields 8 to 17 times better than de novo synthesis, compared to a 1.4 times increase for de novo synthesis in *T. utilis*. One strain produced almost entirely linoleic acid from oleic acid, and this strain appeared best suited for the desaturation of oleic acid to linoleic acid since it had the highest yield, and greatest rate of oleic acid uptake from the fermentation medium. The predominance of fatty acids recovered was similar in all strains, but varied with the substrate, i.e., oleic acid vs. glucose. The yeast strain identified as strain 371, which is a species of the genus Rhodotorula, has been deposited with the American Type Culture Collection under the following ATCC number:

| Strain Number | ATCC Number |
|---|---|
| 371 | 20837 |

The yeast strains of the present invention have desaturase activity for desaturation of fatty acids. For instance, there are three desaturase steps in the fatty acid biosynothetic pathway consisting of stearic (18:0), oleic (18:1), linoleic (18:2) and linolenic (18:3). However, the desaturase yeast strains disclosed herein are particularly suitable for conversion of oleic acid to linoleic acid and the invention is described with respect to that preferred embodiment.

In providing the novel yeast strains of the present invention, water and soil samples were obtained from areas which appeared to have the highest probability for containing microorganisms adapted to the desaturation of fatty acids. These samples were then inoculated into the selective enrichment medium for oleaginous yeast. Novel enrichment medium and cultural conditions were designed for this process and described hereinafter. The approach used in developing the present invention was different from the approach used by the prior art in that the yeasts were isolated for the specific task of desaturating carboxylic acids with high yields compared to the best microorganisms known. Heretofore, yeasts were isolated selectively on the basis of fat content with little regard for production of a specific fatty acid or lipid. In isolating the yeast, the water and soil samples were screened for desaturase activity by the lipoxygenase assay. Since no direct measurement of desaturase enzyme activity existed, the total amount of linoleic acid was used as an indication of desaturase activity since it could only be formed through the action of such an enzyme. *T. utilis* ATCC 8205 was used as the standard. This yeast possesses 1.24 pg linoleic acid/cell and this value was the benchmark for comparison with all other strains. Nearly 50% (94) of the random yeast isolates had desaturase activity greater than the standard. Two of these strains, identified as numbers 238 and 371 were then examined further for desaturase activity and fatty acid composition and yield.

These two yeast strains had linoleic acid contents of 62 and 36 pg/cell respectively when grown on solid agar medium and these were the strains chosen for comparison with the standard. Strains 238 and 371 were identified as Rhodotorula sp. Both strains were grown in a minimal broth medium containing technical grade oleic acid. After three days of incubation, during which time desaturase activity should have been completed, the yeast cells were then analyzed by three analytical procedures to determine their desaturase activity, linoleic acid yield and total fatty acid content and distribution.

In one technique, desaturase activity was determined on the basis of cell yield of linoleic acid using three different analytical methods. The assay techniques were identified as the lipoxygenase technique, the HPLC or high pressure liquid chromatography technique, or the GLC, which is the gas liquid chromatography technique. The results are set forth in the following Table 1. From Table 1 it will be noted that the yeast isolates Nos. 238 and 371 showed a 6.5-fold and a 3-fold respectively increase in desaturase enzyme activity over the standard, which is the *T. utilis* ATCC 8205, when the yeasts were grown in the presence of added oleic acid. In the absence of added oleic acid, i.e., de novo synthesis of linoleic acid from carbohydrate, the desaturase activity of these isolates was lower or equivalent to *T. utilis* ATCC 8205.

TABLE 1

Desaturase Enzyme Activity as Determined by Linoleic Acid Yield (pg/cell) According to Three Different Analytical Methods[a]

| Strain | Oleic Acid Added | Assay Technique | | |
|---|---|---|---|---|
| | | Lipoxygenase | HPLC | GLC |
| *T. utilis* ATCC 8205 | + | 0.82 | 0.75 | 1.13 |
| | − | 0.60 | 0.55 | 0.19 |
| 238 | + | 4.71 | 4.89 | 2.21 |
| | − | 0.28 | 0.24 | 0.14 |
| 371 | + | 2.75 | 2.29 | 2.91 |
| | − | 0.36 | 0.24 | ND[b] |

[a]Yeast grown in broth culture medium.
[b]Not detected.

The conversion of the oleic acid to various fatty acids and yield of linoleic acid was determined for *T. utilis* ATCC 8205 and the yeast isolates grown in broth culture. It was found that the conversion of added oleic acid to linoleic acid was the same, ca. 24 pg/cell, for *T. utilis* ATCC 8205 and strains 238 and 371. Conversion of de novo oleic acid to linoleic acid was 50% lower in strains 238 and 371 compared to *T. utilis* ATCC 8205. However, actual yield of linoleic acid from added oleic acid was 3- to 6-fold higher in strains 238 and 371 than in *T. utilis* ATCC 8205, for example 4.89 and 2.29 vs 0.75 pg/cell respectively. The results are set forth as follows in Table 2.

TABLE 2
Yeast Desaturation of Oleic Acid: Conversion and Yield in Broth Culture Medium

| Strain | Oleic Acid Addition | Oleic Acid Conversion (%)[a] | | | Linoleic Acid Yield (pg/cell) |
|---|---|---|---|---|---|
| | | Linoleic Acid | Linolenic Acid | Polyunsaturates | |
| *T. utilis* | + | 24 | 23 | 47 | 0.75 |
| ATCC 8205 | − | 21 | 7 | 28 | 0.55 |
| 238 | + | 23 | N.S. | 23 | 4.89 |
| | − | 10 | 3 | 13 | 0.24 |
| 371 | + | 24 | 11 | 35 | 2.29 |
| | − | 9 | 2 | 11 | 0.24 |

[a]Since all polyunsaturated fatty acids must originate from oleic acid, the total amount of oleic acid available for conversion is the sum of oleic acid, linoleic acid and linolenic acid in the cell. Thus, the oleic acid conversion calculations were:

$$\frac{18:2}{18:1 + 18:2 + 18:3}, \frac{18:3}{18:1 + 18:2 + 18:3} \text{ and } \frac{18:2 + 18:3}{18:1 + 18:2 + 18:3}$$

[b]N.S., not significant.

The yields of individual fatty acids, total unsaturated fatty acids and total fatty acids from yeast broth cultures of the same strains were determined by high pressure liquid chromatography. It was found that strain 238 was superior to all other yeasts tested for total fatty acids, total unsaturated fatty acids and linoleic acid yield when grown in the presence of added oleic acid. Total fatty acid yield from added oleic acid increased 3- to 6-fold in strains 238 and 371, but remained constant or decreased in *T. utilis* ATCC 8205. Total fatty acid yield from de novo synthesis was the same in all strains except No. 238, which was 2-fold higher. Total polyunsaturated fatty acid yields showed a similar pattern. These results are shown in the following Table 3.

It was found that individual fatty acids varied in quantity from strain to strain and whether or not the yeasts were grown in the presence of added oleic acid. Strains 238 and 371 showed very high increases in oleic acid and linoleic acid, for example, 8 and 20 fold and 3 and 10 fold, respectively when cultured with added oleic acid. An 18 fold increase in linolenic acid was found in strain 371 when grown on oleic acid. These dramatic increases in unsaturated fatty acids were reflected in the total fatty acid yields which increased 3 to 4 fold over de novo synthesis of fatty acids and were 3 to 7 fold higher than *T. utilis* ATCC 8205 grown in the presence of added oleic acid. Quantities of individual fatty acids and total fatty acids were similar in both strains for de novo synthesis.

TABLE 3
Individual and Total Fatty Acid Yields from Yeast Grown in Broth Culture Medium as Determined by HPLC

| Strain | Oleic Acid Addition | Fatty Acid (pg/cell) | | | | | Total Unsaturates | Total Fatty Acids |
|---|---|---|---|---|---|---|---|---|
| | | Palmitic (16:0) | Stearic (18:0) | Oleic (18:1) | Linoleic (18:2) | Linolenic (18:3) | | |
| *T. utilis* | + | 0.39 | 0.026 | 1.64 | 0.75 | 0.73 | 3.12 | 3.54 |
| ATCC 8205 | − | 0.43 | 0.022 | 1.85 | 0.55 | 0.17 | 2.57 | 3.02 |
| 238 | + | 2.79 | 0.19 | 16.61 | 4.89 | 0.002 | 21.50 | 24.48 |
| | − | 3.69 | 0.067 | 1.9 | 0.24 | 0.07 | 2.30 | 6.06 |
| 371 | + | 1.27 | 0.059 | 7.01 | 2.29 | 1.07 | 9.37 | 10.70 |
| | − | 0.53 | 0.084 | 2.49 | 0.24 | 0.06 | 2.79 | 3.40 |

However, strain 238 showed a high concentration of palmitic acid compared to the other strains tested. This resulted because the total fatty acid yield of strain 238 was 2 fold higher than the other strain. Thus, the disclosed yeast isolates were superior to *T. utilis* ATCC 8205 in several ways. When cultured in the presence of oleic acid, strains 238 and 371 had greater desaturase enzyme activity as measured by linoleic acid content, both strains demonstrated efficient uptake mechanisms for incorporating oleic acid from the liquid medium, and the level of oelic acid in these strains was 4 to 10 fold higher than in *T. utilis* ATCC 8205. Desaturase enzyme activity and fatty acid yields were inducible to high levels by the addition of oleic acid. In contrast, *T. utilis* ATCC 8205 was poorly stimulated by oleic acid and yields of all fatty acids were significantly lower than strains 238 and 371. The following Table 4 lists the properties of yeast desaturation of added oleic acid.

TABLE 4
Distribution of $^{14}$C-Oleic Acid (%) in Yeast Isolates

| $^{14}$C-oleic Acid | PO$_4$ Buffer[a] | | YPD[b] | |
|---|---|---|---|---|
| | 238 | 371 | 238 | 371 |
| Incorporated | 77 | 72 | 81 | 77 |
| Free | 10 | 16 | 17 | 17 |
| Adsorbed (Sum of 4 Washes w/5% MeOH—H$_2$O) | 12 | 11 | 2 | 6 |

[a]Incubation of 3 hours.
[b]YPD, yeast extract-proteose peptone-dextrose broth; Incubation for 24 hours.

The culture medium preferably used with the yeast strains of this invention is a novel culture medium and generally comprises a mixture of certain basal salts, nutrients and antibiotics. In general, the culture medium may be described as a mixture of basal salts and nutrients, combined with an antibiotic solution. The basal salts and nutrient mixture generally comprises glucose, a yeast extract, buffering salts and alkaline earth metal salts; in particular, magnesium sulfate and calcium chloride in their hydrated forms. The preferred basal salt mixture will contain glucose, a yeast extract, ammonium sulfate, potassium dihydrogen phosphate, disodium hydrogen phosphate, magnesium sulfate and calcium chloride in their hydrated forms. This basal salt mixture is combined with an antibiotic solution which contains 1-10 mg.% of appropriate antibiotics. These materials are primarily antibiotics of the class selected from the group consisting of tetracycline, chloratetracycline, chloramphenicol, streptomycin, and fungizone, and mixtures thereof. Preferably, the antibiotic solution contains chlorotetracycline, chloramphenicol, streptomycinsulfate, and fungizone. The pH of this mixture is adjusted to the range of 4.3 to 4.7, preferably 4.5, by the addition of an acid.

The preferred yeast culture medium of this invention comprises the following formulation which has a pH of 4.4–4.6:

| YEAST CULTURE MEDIUM (YIM) | | |
|---|---|---|
| A. | Basal Salts and Nutrients | |
| | Glucose | 2–5 wt. % |
| | Yeast Extract | 0.02–0.08 wt. % |
| | $(NH_4)_2SO_4$ | 0.05–0.02 wt. % |
| | Alkali metal phosphates | 0.5–1.5 wt. % |
| | Alkaline earth metal salts | 0.08–0.2 wt. % |
| B. | Antibiotics Solution | 1–10 mg. % |

In this formulation, the alkali metal phosphates are buffers and are preferably mixtures of $Na_2HSO_4$, $NaH_2PO_4$, $KH_2SO_4$ and/or $KH_2PO_4$. The alkaline earth metal salts are preferably magnesium and calcium salts, such as the halides, sulfates, and the like.

A highly preferred yeast culture medium is the following formulation which has a pH of about 4.5:

| YEAST CULTURE MEDIUM (YIM) | | |
|---|---|---|
| A. | Basal Salts and Nutrients | |
| | Glucose | 3 wt. % |
| | Yeast Extract | 0.05 wt. % |
| | $(NH_4)_2SO_4$ | 0.1 wt. % |
| | $KH_2PO_4$ | 0.7 wt. % |
| | $Na_2HPO_4$ | 0.2 wt. % |
| | $MgSO_4.7H_2O$ | 0.15 wt. % |
| | $CaCL.6H_2O$ | 0.02 wt. % |
| B. | Antibiotics Solution | |
| | Chloratetracycline | 1 mg. % |
| | Chloramphenicol | 2 mg. % |
| | Streptomycin-sulfate | 2 mg. % |
| | Fungizone | 1 wt. % |

In this formulation, the pH is adjusted to 4.5 with lactic acid or HCl.

The enrichment and isolation process is also conducted under unique incubation conditions. Thus, incubation is carried out at a temperature of 20°–25° C. or more preferably, a one day incubation at about 30° C. and a second day incubation at about 20°–25° C. The lower temperatures induce yeast metabolism of fatty acids or normal alkanes to produce fat-rich conditions in the yeast cell. This induction process is required for the yeast to maintain membrane fluidity and growth at the lower temperatures. Therefore, when the selective nature of the culture medium is combined with the unique incubation temperatures, there is an enrichment in selection for oleaginous yeast that is not obtained with other methods with any significant success.

In analyzing these yeast cultures, no bacteria or fungi were detected in the enrichment broth cultures and on the conventional or selective media inoculated with enrichment broth culture samples. Thus, the unique composition of the enrichment broth culture medium in incubation conditions were effective in selecting for yeasts in fostering their growth.

As pointed out, the yeast strains of the invention and their equivalents, are useful for desaturation of fatty acids such as the conversion of oleic acid to linoleic acid. Particularly preferred results are obtained using the yeast culture medium described herein. However, it will be understood that other operative yeast culture media may be used in practice of the invention. Further, the fatty acid to be desaturated may be pure or contained in admixture with other materials. The invention is particularly applicable to upgrading tall oil fractions. These fractions contain both oleic and linoleic acid but a more valuable fraction is obtained if the linoleic acid content is increased. The present invention provides a novel and efficient procedure for such conversions.

It will be understood that the invention is described herein with respect to the specific strains identified as species of Rhodotorula. However, it will be understood that the invention is also inclusive of equivalent and similar microorganism strains which have the identifying characteristics and desaturase activity of these strains.

The invention described herein is significant in that yeasts were isolated for the specific task of desaturating oleic acid to linoleic acid with high yields, compared to the best microorganisms known. Until now all researchers selectively isolated yeast on the basis of fat content with little regard for production of a specific fatty acid or lipid. Thus, manipulation of fermentation conditions to favor the production of the desired product was important in the work described herein.

In the Examples described hereinbelow, T. utilis ATCC 8205 was obtained from the American Type Culture Collection. Oleaginous yeast isolates were obtained by selective enrichment culture from soil and water samples, enriched and isolated as described herein. Selected yeast isolates were identified according to the procedures given in the Handbook of Microbiology, (1974) pp. 395–433, CRC Press, Cleveland, Ohio.

Since no direct assay existed for the measurement of desaturase enzyme activity, an indirect measure was made by quantitation of linoleic acid and linolenic acid, the end-products of the desaturase reaction. Yeasts were grown overnight on agar of the yeast culture medium (YIM) described hereinbefore which contained 10% (v/v) oleic acid, and ca. $1 \times 10^8$ cells were removed for saponification in 1 ml 1.5 N ethanolic KOH overnight. The pH of the cell suspension was adjusted to ca. 9 with 6N HCl and 5 ml. of 1 M potassium borate buffer (pH 9) was added prior to centrifugation to remove insoluble material. 0.3 ml of saponified cell extract was added to 2.7 ml 0.2 M potassium borate buffer (pH 9) in duplicate. One solution (reference cell) received 100 μl of heat inactivated soybean lipoxygenase (Sigma Type I, 0.2 mg/ml in 0.2 M potassium borate buffer, pH 9.0) and the sample cell received the same quantity of active enzyme. The absorbance of each solution at 234 nm was monitored over one minute in a spectrophotometer, and the result expressed as total polyunsaturated fatty acid (PFA). Desaturase activity was calculated as the pg. of linoleic acid equivalents per yeast cell based on a molar extinction coefficient of 21,900.

For purposes of comparison, the linoleic acid content and fatty acid composition of the selected yeast strains were analyzed by gas-liquid chromatography (GLC) and high pressure liquid chromatography (HPLC). The saponified cell extracts were acidified to pH 1–2 with 1N HCl and extracted with 2 ml hexane. Aliquots of the hexane layers were evaporated to dryness with a stream of nitrogen. The free fatty acids were converted to the methyl esters by tetramethyl ammonium hydroxide in MeOH using phenolphthalein as an indicator for GLC analyses. Heptadecanoic acid was added as an internal standard. For HPLC analyses, the free fatty acids were converted to the phenacyl esters. The phenacyl esters were separated on a Waters 'Fatty Acid' column using THF:$CH_3CN$:$H_2O$: HOAC=3:61:36:0.1 (v/v) as the mobile phase and a flow rate of 2 ml/min. Good separations of the fatty acids were achieved with the exception of palmitoleic acid and linolenic acid which co-eluted under these conditions.

Desaturase activity, fatty acid composition, and de novo synthesis of linoleic acid in the two lipid-rich yeasts and T. utilis ATCC 8205 were determined from shake-flask broth cultures. All four strains were subcultured from YPD agar stock slants to 50 ml YIM broth incubated overnight at 30° C. with 200 rpm shaking. The overnight cultures were harvested, resuspended in an equivalent volume of phosphate buffer, and inoculated into flasks containing YIM broth with no oleic acid (de novo synthesis), 0.5 uCi [1-$^{14}$C]-oleic acid (desaturation of pure oleic acid) and tests were run in duplicate and incubated 72 hours at 30° C. with 200 rpm shaking. The number of yeast cells in each culture was determined by the spread plate technique on yeast extract-potato dextrose agar. Desaturase activity and fatty acid analysis were determined as given above. $^{14}$C-linoleic acid was analyzed by a procedure described herein.

The YPD agar medium is described in the Examples. The YIM broth is the novel culture medium described hereinbefore.

The following Table 5 is a summary of the results obtained in these studies in desaturation of added oleic acid for desaturase conversion.

TABLE 5

Comparison of Fatty Acid Yields with Batch Fermentation

| Strain | Linoleic Acid Yield (g/l) Added Oleic Acid | Linoleic Acid Yield (g/l) de novo | de novo Yield of Polyunsaturates (g/l) |
|---|---|---|---|
| T. utilis ATCC 8205 | 0.38 | 0.28 | 0.36 |
| 238 | 2.45 | 0.12 | 0.16 |
| 371 | 1.15 | 0.12 | 0.15 |
| Theoretical Maximum[a] | 16.0 | | |
| Suzuki et al.[b] | | | 0.66 |

[a]Assuming biomass yield of 50 gdw/l, 40% lipid content, 80% of lipid as linoleic acid (see Ref. 10 and 11)
[b]Fungus, *Pellicularia filamentosa* No. 6295 (U.S. Pat. No. 4,281,064).

The following examples are presented to illustrate the invention. However, as obvious variations thereon will become apparent to those skilled in the art, the invention is not to be considered as limited thereto. In the examples and throughout the specification, parts are by weight unless otherwise indicated.

EXAMPLES

Five water samples and one soil sample were taken under environmental conditions which appeared to have a high probability of including microorganisms adapted for the desaturation of fatty acids. These samples were analyzed individually for total yeast and total microorganisms, i.e., bacteria, yeast and fungi, and more than 2,000 separate yeast strains were isolated and tested for desaturase activity.

In a first set of experiments, portions of each sample were inoculated into a conventional culture medium (YPD) and analyzed for total number of yeast and total microorganisms. Other portions of each sample were inoculated into a selective enrichment medium (LYIM) and analyzed for total yeast and for fatty acid utilizing (hyper-desaturase) yeasts. The conventional culture medium (YPD) comprised a solution of about 2% glucose, 1% yeast extract and 2% peptone with the pH adjusted to 5.6 with HCl. The selective enrichment medium (LYIM) comprised a solution preferred yeast culture medium (YIM) described hereinbefore, supplemented with 20% of a tall oil sample containing about 1% rosin acid. The yeast culture medium (YIM) was prepared by first preparing the basal salt medium by mixing the listed ingredients, adjusting the pH to 4.5 with the addition of acid, and filter sterilizing. The antibiotic solution, which contained the indicated amount in milligrams per 100 ml of total solution was filter sterilized with moderate vacuum pressure and added to the cool basal salt nutrient mixture. Using this mixture, the culture medium (YIM) was selectively enriched with the addition of about 20% of the tall oil sample. The tall oil sample was added in a final concentration (v/v) of 1% to the basal salt's nutrient solution for agar media and in total percent amounts for broth media. The tall oil sample was emulsified for the agar medium by sonication for thirty minutes prior to sterilization. In the yeast enrichment process, 30 ml of the (LYIM) broth medium containing 20% of the tall oil sample was inoculated with 10 ml of water sample or 10 ml of the 1:10 dilution of soil sample and phosphate buffer. All inoculated broths were incubated at 25° C. with ca. 200 rpm shaking for 24 hours. Yeasts were isolated and enumerated by serial dilution of the enrichment broth cultures onto the conventional yeast culture medium (YPD) spread plates and the selective enrichment yeast culture medium (LYIM) spread plates. Inoculated plates were incubated at 25° C. for 24-48 hours and identification of colonies as yeast was done by microscopic wet mount observation of random colonies.

The recovery of yeast relative to total aerobic heterotrophs was variable but within the same order of magnitude. However, microscopic observation showed that many of the colonies growing on the conventional (YPD) medium agar were bacteria, not yeast. Thus, the total yeast count for these samples is an overestimate due to the non-selective nature of the conventional (YPD) medium.

The enrichment broth culture for each sample was found to contain high numbers of yeast when assayed on the conventional medium and the novel selective medium. No bacteria or fungi were detected in the enrichment broth cultures and on the conventional or selective media inoculated within enrichment broth culture samples. Thus, the unique composition of the enrichment medium and incubation conditions were totally effective in selecting for yeasts and fostering their growth. In this instance where only yeast were present in the sample enrichment broth cultures, the conventional culture medium agar was comparable to the novel yeast medium in recovering yeast.

The numbers of yeasts and fatty acid utilizing yeasts were highest in the enrichment broth cultures of samples which were heavily contaminated by fatty acids and had an acid pH, which are conditions favorable to the growth of yeast. After two days of incubation, the fatty acid component of all of the enrichment broth cultures was completely emulsified by the yeast.

It was concluded from these experiments that oleaginous and oil emulsifying yeasts could be isolated in pure culture directly from soil and water samples using the selective enrichment culture medium and process. The results of these experiments is shown in Table 6.

TABLE 6

Enumeration of Oleaginous Yeast and Fatty Acid Utilizing Yeast[a]

| Sample | pH | Raw Sample | | (LYIM) Culture Medium | |
|---|---|---|---|---|---|
| | | Total Microorganisms[b] | Total Yeast[c] | Total Yeast[c] | Fatty Acid Utilizing Yeast[d] |
| 1 | 3.34 | 2.0 | 1.17 | 5.3 | 6.3 |
| 2 | 6.70 | 3.3 | 1.9 | 5.0 | — |
| 3 | 7.16 | 1.0 | 1.7 | 7.5 | 7.6 |
| 4 | 4.77 | 0.7 | 1.1 | 4.8 | 8.0 |
| 5 | 3.41 | 0.9 | 3.2 | 35.0 | 68.0 |
| 6[e] | — | 15.0 | 8.0 | 28.0 | 45.0 |

[a] Colony-forming Units ($\times 10^6$/ml or gww sample)
[b] Bacteria, Yeast and fungi
[c] Enumerated with yeast-potato-dextrose sugar
[d] Enumerated with (LYIM) culture medium
[e] Soil Sample In a second set of experiments, the 2,000 yeast isolates obtained from selective enrichment cultures of the water and soil samples were screened for desaturase activity by the lipoxygenase assay. Since no direct measurement of desaturase enzyme activity existed, the total amount of linolenic acid was determined for comparative purposes. *T. utilis* ATCC 8205 possessed 1.24 pg linoleic acid/cell by this method, and this value was used as the benchmark for comparison with all other strains. From this study, nearly 50% (94) of 200 random yeast isolates were found to have a desaturase activity greater than *T. utilis* ATCC 8205. Eighteen, or about 10% of the yeast isolates tested had desaturase activities more than 10 times that of the reference strain. Two of these strains, Nos. 238 and 371 were selected for further examination of desaturase activity, fatty acid composition and yield by the three analytical techniques. Distribution of the yeast isolates on the basis of desaturase activity and the site of origin for culture inoculum were also studied. It was found that environmental differences, such as pH, water, soil, temperature, extent of fatty acid contamination, etc. of the various samples did not substantially influence the distribution of the yeast. However, about two-thirds of the yeast strains had a linoleic acid content greater than 3.0 pg/cell. Most of the strains were identified as being from the genus Torolupsis or Rhodotorula.

The two strains selected for further study and comparison with *T. utilis* ATCC 8205 were compared for desaturase activity as described herein with respect to the results shown in Tables 1-4. As indicated, these strains were identified as of the genus Rhodotorula, species Nos. 238 and 371. The yeast culture medium used to evaluate these yeast strains was the preferred yeast culture medium (YIM) described hereinbefore.

Each of the strains identified as species Nos. 238 and 371 together with *T. utilis* ATCC 8205 were cultured in the presence of oleic acid using the (YIM) culture medium. In this process, it was found that strains 238 and 371 had 10 to 20 times the desaturase activity of the standard *T. utilis* ATCC 8205, as measured by the linoleic acid content. Both of these strains demonstrated efficient uptake mechanisms for incorporating oleic acid from liquid medium. The level of oleic acid in these strains was 4-10 fold higher than in the known *T. utilis* ATCC 8205. Desaturase enzyme activity and fatty acid yields were inducible to high levels by the addition of the oleic acid. In contrast, *T. utilis* ATCC 8205 was poorly stimulated by oleic acid and yields of all fatty acids were significantly lower than for strains No. 238 and 371. The data in Table 7 shows the properties of the yeast desaturation of the added oleic acid.

TABLE 7

Properties of Yeast Desaturation of Added Oleic Acid

| Parameter | T. utilis ATCC 8205 | Strain No. 238 | Strain No. 371 |
|---|---|---|---|
| Linoleic Acid Yield (pg/cell) | 0.8 | 4.9 | 2.3 |
| Oleic Acid Conversion (%) | 24 | 23 | 24 |
| Oleic Acid Uptake (pg/cell) | 1.6 | 16.6 | 7.0 |
| 18:2/18:1 | .46 | 4.9 | .33 |
| Total Polyunsaturates (pg/cell) | 1.5 | 4.9 | 3.4 |
| Mixture of Polyunsaturates | Yes | No | Yes |
| Total Fatty Acids (pg/cell) | 3.5 | 24.5 | 10.7 |

While the conversion efficiencies for strains 238 and 371 are lowest, these strains had the highest yield of unsaturated fatty acids, i.e., 18:1, 18:2 and 18:3. Strain 238 produced almost entirely linoleic acid from oleic acid and strain 371 synthesized 68% linoleic acid and 32% linolenic acid. These high yields are most likely due to efficient uptake mechanisms for oleic acids since the level of 18:1 parallels the increase in total polyunsaturates.

The invention has been described herein with reference to certain preferred embodiments. However, as obvious variations thereon will become apparent to those skilled in the art, the invention is not to be considered as limited thereto.

What is claimed is:

1. A biologically pure culture of the microorganism Rhodotorula, which has the identifying characteristics of the strain ATCC No. 20837.

* * * * *